United States Patent
Liu

(10) Patent No.: US 11,852,757 B2
(45) Date of Patent: Dec. 26, 2023

(54) PET DETECTOR FOR REDUCING NUMBER OF SILICON PHOTOMULTIPLIERS IN USE AND DETECTION METHOD

(71) Applicant: SHANDONG MADIC TECHNOLOGY CO., LTD., Linyi (CN)

(72) Inventor: Jiguo Liu, Linyi (CN)

(73) Assignee: SHANDONG MADIC TECHNOLOGY CO., LTD., Linyi (CN)

(*) Notice: Subject to any disclaimer, the term of this patent is extended or adjusted under 35 U.S.C. 154(b) by 411 days.

(21) Appl. No.: 17/299,534

(22) PCT Filed: Apr. 1, 2019

(86) PCT No.: PCT/CN2019/080782
§ 371 (c)(1),
(2) Date: Jul. 8, 2021

(87) PCT Pub. No.: WO2020/113872
PCT Pub. Date: Jun. 11, 2020

(65) Prior Publication Data
US 2022/0057532 A1    Feb. 24, 2022

(30) Foreign Application Priority Data
Dec. 4, 2018   (CN) .......................... 201811474960.6

(51) Int. Cl.
*G01T 1/164* (2006.01)
*A61B 6/03* (2006.01)
*G01T 1/208* (2006.01)

(52) U.S. Cl.
CPC .......... *G01T 1/1644* (2013.01); *A61B 6/037* (2013.01); *G01T 1/208* (2013.01)

(58) Field of Classification Search
CPC ..... G01T 1/1644; G01T 1/208; G01T 1/1642; G01T 1/2985; A61B 6/037
See application file for complete search history.

(56) References Cited

U.S. PATENT DOCUMENTS

| 10,267,931 B1* | 4/2019 | Breuer ................. G01T 1/2008 |
| 2012/0061577 A1 | 3/2012 | Oleinik et al. |

(Continued)

FOREIGN PATENT DOCUMENTS

| CN | 101644780 A | 2/2010 |
| CN | 101833106 A | 9/2010 |

(Continued)

OTHER PUBLICATIONS

Extended European Search report dated Jul. 12, 2022 received in European Patent Application No. EP 19893956.3.

(Continued)

*Primary Examiner* — Kiho Kim
(74) *Attorney, Agent, or Firm* — Scully, Scott, Murphy & Presser, P.C.

(57) ABSTRACT

Provided is a PET detector for reducing the number of silicon photomultipliers in use, which is characterized in that: the detector comprises layers respectively formed by a scintillation crystal array unit and a silicon photomultiplier (4) array unit, the scintillation crystal array unit and the silicon photomultiplier (4) array unit are rectangular cross sections in plan view, and the scintillation crystal array unit and the silicon photomultiplier (4) array unit have the same area of the rectangular cross sections in plan view; the scintillation crystal array unit consists of a plurality of scintillation crystal strips (1) parallel to each other, free of gaps and attached to each other on sides, the scintillation crystal strips (1) are all cuboids with uniform length, width and height; the silicon photomultiplier (4) array unit is an array assembly, which is formed by M silicon photomulti- (Continued)

plier (4) arrays and has the rectangular cross section in plan view.

7 Claims, 3 Drawing Sheets

(56) References Cited

U.S. PATENT DOCUMENTS

| | | | |
|---|---|---|---|
| 2014/0209804 A1* | 7/2014 | Lee | G01T 1/2985 250/362 |
| 2015/0285923 A1* | 10/2015 | Tonami | G01T 1/248 250/368 |
| 2018/0172847 A1 | 6/2018 | Nelson et al. | |

FOREIGN PATENT DOCUMENTS

| | | |
|---|---|---|
| CN | 102707310 A | 10/2012 |
| CN | 204118095 U | 1/2015 |
| CN | 104570042 A | 4/2015 |
| CN | 105655435 A | 6/2016 |
| CN | 105759301 A | 7/2016 |
| CN | 106443757 A | 2/2017 |
| CN | 107110981 A | 8/2017 |
| CN | 107167832 A | 9/2017 |
| CN | 107728188 A | 2/2018 |
| CN | 109856665 A | 6/2019 |
| JP | 5585094 B2 | 9/2014 |

OTHER PUBLICATIONS

International Search Report dated Sep. 2, 2019 issued in PCT/CN2019/080782.
Chinese Office Action dated May 25, 2020 issued in CN 201811474960.6.

* cited by examiner

PET DETECTOR FOR REDUCING NUMBER OF SILICON PHOTOMULTIPLIERS IN USE AND DETECTION METHOD

TECHNICAL FIELD

The present disclosure relates to the field of radiographic medical imaging equipment, and relates to a PET detector for reducing the number of silicon photomultiplier tubes in use and a detection method. The method can be applied to medical imaging equipment including PET, SPECT and those with similar principles.

BACKGROUND

In nuclear medicine imaging equipment such as PET and SPECT, it is required to measure the position and energy of rays. PET is the most typical medical imaging method that collects oppositely reflected photoelectrons (generally called true coincidence event LOR (line of reaction) and analyzes them accordingly to form an image. At present, the most common PET detector is a scintillator detector plus a photoelectric conversion device. After the rays hit scintillators, scintillation fluorescence is generated. The scintillation fluorescence is converted into an electrical signal by the photoelectric conversion device, and then sent to an electronic system for processing.

Commonly used photoelectric conversion devices include photomultiplier tubes, position-sensitive photomultiplier tubes and silicon photomultiplier tubes. The silicon photomultiplier tube is a semiconductor photoelectric conversion device that has become popular in recent years. The effect of the silicon photomultiplier tube is better than the photomultiplier tube and the position-sensitive photomultiplier tube, and the gain is close to that of the photomultiplier tube. It can be a single pixel at the time of purchase, or it can be an array of N×N (N≥2) pixels, with the pixel size generally being 1 mm-10 mm. The silicon photomultiplier tube array is very similar in function to the position-sensitive photomultiplier tube, but it outputs signals in a way in which each pixel outputs a signal, which has a stronger recognition and positioning ability. The silicon photomultiplier tube array is similar in function to the position-sensitive photomultiplier tube, and the price is close to that of the photomultiplier tube. As a semiconductor device, there is room for further drop in the price of the silicon photomultiplier tube in case of mass production.

The design of PET detectors based on photomultiplier tubes can be divided into two types. One is to use 4 photomultiplier tubes combined with one scintillation crystal array (U.S. Pat. Nos. 4,743,764, 5,453,623, 6,262,479B1, U.S. Pat. No. 7,238,943B2), in which the crystal luminescence collected from 4 photomultiplier tubes is used to calculate the positions where the rays hit the detector; and the other is to arrange the photomultiplier tubes in a hexagonal shape (U.S. Pat. No. 6,462,341B1), in which the crystal luminescence collected from 7 photomultiplier tubes is used to calculate the positions where the rays hit the detector.

There are two ways to read out a signal of the photomultiplier tube. One is to directly digitize, and the other is to encode through the ANGER circuit (U.S. Pat. No. 3,011,057) and then digitize. The use of silicon photomultiplier tube is mainly the latter one, which facilitates taking advantage of its signal reception and transmission respectively. After being processed by the ANGER circuit, an output signal of a group of photomultiplier tubes can be encoded into three analog signals E, X and Y, so as to achieve the purpose of reducing the circuit scale.

There is such a solution in the prior art (CN201410648328.4), in which a layer of light guides is added between a crystal array and a silicon photomultiplier tube array, and the light is distributed with the aid of the light guides, with the purpose of being able to identify crystals smaller than the pixels of the silicon photomultiplier tubes and improve the resolution. However, the addition of the light guides in the prior art is only used for general auxiliary light distribution, and there is no further specific enlightenment or instruction.

There are also two ways to read out a signal of the silicon photomultiplier tube. One is to read out each pixel and then digitize it. The other way is to use an analog preprocessing circuit (CN201410648328.4) to preprocess a signal of the silicon photomultiplier tube array. Through the preprocessing, the signal of one array can be encoded into a minimum of 4 analog signals to achieve the purpose of reducing the circuit scale.

At present, the number of crystals in a common human body PET is more than 30,000, and can exceed 100,000 at the most, in which more than 30,000 silicon photomultiplier tube pixels are used. Generally, the commercially available silicon photomultiplier tube arrays are 2×2, 4×4 or 8×8, mainly 4×4. Taking 32,000 crystals as an example, it is assumed that approximately each crystal corresponds to one pixel, then the device needs 2,000 4×4 silicon photomultiplier tube arrays. Even if after encoding, the number of analog signal channels can still reach 8,000, and the circuit scale is very large. At the same time, due to the huge amount, the total cost is still very high. How to effectively control the circuit scale and reduce equipment costs is still a huge challenge.

SUMMARY

In view of the above problems of very large amount and extremely high cost of silicon photomultiplier tubes used in the prior art, the present disclosure provides a PET detector for reducing the number of silicon photomultiplier tubes in use, in which: the detector includes a layer formed by scintillation crystal array units and a layer formed by silicon photomultiplier tube array units respectively, the scintillation crystal array units and the silicon photomultiplier tube array units each have a rectangular cross section in the top view, and the top-view rectangular cross sections of the scintillation crystal array units and the silicon photomultiplier tube array units have the same area.

Herein, preferably, each scintillation crystal strip corresponds to exactly one pixel or one pixel array, which is a situation where it is easier to collect and calculate.

The scintillation crystal array unit is composed of a plurality of mutually parallel scintillation crystal strips, the scintillation crystal strips are each rectangular parallelepipeds having the same specifications in terms of each of the length, the width and the height, and each two of the scintillation crystal strips are provided with a reflective material therebetween or surfaces of the scintillation crystal strips are plated with a reflective material.

The silicon photomultiplier tube array unit is an array aggregate with a rectangular cross section in the top view formed by arranging M silicon photomultiplier tube arrays. Of course, when the demand of the unit is the same as that of a general silicon photomultiplier tube array, it may be a silicon photomultiplier tube array, such as 4*4/8*8, and when a larger array can be customized and processed, a larger monolithic array may also be directly arranged for the array unit. A common practice is arranging square arrays into a larger square array unit.

N blocks in the silicon photomultiplier tube array unit are replaced with high-reflectivity material blocks, and the high-reflectivity material block is integrally formed by using a mold adapted to the shape of the silicon photomultiplier tube array unit, or is formed by cutting. The high-reflectivity material block is made entirely of a uniform high-reflectivity material, or a side of the high-reflectivity material block that faces the scintillation crystal array unit is coated with a high-reflectivity material, and the reflectivity of the side of the high-reflectivity material block that faces the scintillation crystal array unit is not less than 50%.

Herein, the high-reflectivity material is a high-reflectivity material suitable for reflecting excited fluorescence, and the reflectivity can be as high as 70%, 80%, 90%, or even close to 100%. Herein, some silicon photomultiplier tube arrays are replaced with the high-reflectivity material, and this is based on the following principle: the existing PET image analysis does not and does not need to reach the image level of HD or even UHD; especially during the calculation, if the calculation is not performed separately for each pixel or each array of the silicon photomultiplier tube, but for each unit separately, then in fact, there is no need to wholly lay or apply silicon photomultiplier tubes. Herein, only part of the arrays needs to be replaced with the high-reflectivity material. For the case where the entire unit uses one circuit to form one signal output, it is herein sufficient to meet the needs, and the cost is also effectively controlled while meeting the needs. If only four corners of the arrays are reserved for the case of 3*3, the cost can be saved by 5/9. For the case where the unit is formed by 4*4 arrays, if only the four corners are reserved, the cost can be saved by 12/16; at the same time, the detection effect is not reduced or missing, and the original excited fluorescence can still be effectively captured.

Both M and N are natural numbers greater than 1, and M-N≥1. Herein, the data setting refers to effective replacement. After all, if there is no replacement, there will be no cost-saving effect.

Further, between the layers formed by the scintillation crystal array units and the silicon photomultiplier tube array units respectively, a layer formed by laying a plurality of light guide sheets flat is further formed. The plurality of light guide sheets are rectangular parallelepipeds of the same shape. The top-view cross section of the light guide sheets is rectangular. Providing the light guide layer not only plays a role in assisting light collection, but also produces an interaction for the case of replacing with the high-reflectivity material block. Herein, the fluorescence reflected by the high-reflectivity material block will basically not be reflected back into the crystals due to the characteristics of the light guides. Rather, it is basically ensured that after one or more reflections, the fluorescence will all be collected or received by other silicon photomultiplier tube arrays in the unit.

Further, the reflective material is selected from one of a super-grade retroreflective material, an engineering-grade reflective film, a high-grade reflective film, an enhanced spectrum reflective film, and a barium sulfate coating. The coating/plating made of the enhanced spectrum reflective film (ESR) and barium sulfate powder has better effect in practice, and the cost is not high. If a higher reflection effect is required, the super-grade retroreflective material, the engineering-grade reflective film and the high-grade reflective film may also be used. For example, the super-grade retroreflective material is a prism-grade reflective material. In the most ideal way, all the positions between the scintillation crystal strips have the reflective material to avoid light doping.

Further, the top-view cross-sectional size of the light guide sheets is the same as that of the scintillation crystal strips, and each light guide sheet is aligned with the scintillation crystal strip in the top-view direction during installation; or the top-view cross-sectional size of the light guide sheets is the same as that of the silicon photomultiplier tube arrays, and each silicon photomultiplier tube is aligned with the scintillation crystal strip in the top-view direction during installation. This setting facilitates the calculation and arrangement in the early stage, and also facilitates the maintenance and adjustment in the later stage.

Further, for the contact surfaces of the layer formed by the scintillation crystal array units and the layer formed by laying the plurality of light guide sheets flat, the surfaces of all the scintillation crystal array units are rough surfaces, or the surfaces of all the light guide sheets are rough surfaces. The rough surfaces are all prepared by sanding or filing, or a substance that makes the surfaces rough but still be transparent to light is coated or adhered to the surfaces. The contact surfaces of the scintillation crystals and the light guides here may all be rough surfaces. This is a very important further improvement. This setting can further reduce the influence of light emitting positions on the basis of providing auxiliary light splitting by the light guides. For example, the high-reflectivity material block is located under the light guide sheet below a certain crystal strip, and this position is very far away from the nearest silicon photomultiplier tube array. In the absence of diffuse reflection on the rough surface of the light guide, multiple times of reflection may be required, and the multiple times of reflection cause its energy to be greatly attenuated, which has a very bad influence on the analysis; or a very large part of the light cannot reach the array, which has a great influence on the signal collection. The roughening of the surface is a very important auxiliary means for the general collection of optical signals, especially when part of the array is replaced by the high-reflectivity material block, so that it can be ensured that the effect of signal collection is not affected as much as possible when the array is replaced.

After the replacement, we carried out a comparative test. Under other conditions, in the case where part of the array was replaced, the light guide layer was added, and the contact surfaces between the light guide layer and the crystals were rough, the bitmap effect of the detector did not decrease at all during PET image collection.

A PET detection method is provided, which utilizes the PET detector for reducing the number of silicon photomultiplier tubes in use as described above, and which includes the following steps: 1) taking each of the silicon photomultiplier tube arrays that have not been replaced as a current source, and connecting output terminals of all the silicon photomultiplier tube arrays that have not been replaced in parallel before outputting to total output terminal lines; 2) using the aforementioned PET detector for PET detection, preprocessing electrical signals obtained from the total output terminal lines through a preprocessing circuit, and then digitizing them to obtain output signals; 3) the output signals in step 2) being equivalent to an output signal collected under the situation where the entire silicon photomultiplier tube array unit is taken as an entire silicon photomultiplier tube array; and 4) collecting, by an operational terminal, all the output signals collected from all the aforementioned total output terminal lines, and analyzing the existence of LOR according to a preset correspondence to generate a PET image or a PET dynamic image.

A PET detection method is provided, which utilizes the PET detector for reducing the number of silicon photomultiplier tubes in use as described above, and which includes the following steps: 1) taking each of the silicon photomultiplier tube arrays that have not been replaced as a current source, and connecting output terminals of all the silicon photomultiplier tube arrays that have not been replaced in parallel before outputting to total output terminal lines; 2) using the aforementioned PET detector for PET detection, preprocessing electrical signals obtained from several adjacent total output terminal lines through a preprocessing circuit, and then digitizing them to obtain output signals; 3) the output signals in step 2) being equivalent to an output signal collected under the situation where all the photomultiplier tube array units corresponding to the several adjacent total output terminal lines in step 2) are taken as a separate collection unit; and 4) collecting, by an operational terminal, all the output signals from all the separate collection units obtained through collection, and analyzing the existence of LOR according to a preset correspondence to generate a PET image or a PET dynamic image.

The present disclosure has the following advantages: In the design of the present disclosure, the PET detector for reducing the number of silicon photomultiplier tubes in use and the PET detection method using this detector can effectively reduce the number of silicon photomultiplier tube arrays and the number of signal channels. In reality, for each piece of SiPMTs as provided, it is necessary to set up signal connections and channels for collection, and the SiMPTs themselves are very valuable. As for how to effectively save the cost while ensuring a certain quality of PET detection images, the present application provides an effective solution. The number of signal channels can be further reduced, and the scale of the electronic system can be reduced.

Since part of the SiMPTs is replaced by the high-reflectivity material block, on one hand, the signal will not be lost, or it will still be reflected to a certain SiMPT so that the signal can be collected. Since the size of each pixel is typically of the order of millimeter, if the signal is read out as a whole from several combinations of the high-reflectivity material blocks and SiMPTs for calculation and image generation, since the circuit design is difficult and very complicated in practice, it is in fact basically impossible to read the signal of each pixel. In many cases, multiple pixels were originally read altogether. Therefore, the present application greatly reduces the equipment cost without reducing the image resolution at all.

For this situation of partial replacement with high-reflectivity material, it is very necessary to add light guides, so that some SiPMTs can receive signals better, and the rough surfaces can further enhance the effect, so that the image signal and definition are further enhanced under the same conditions. This is not disclosed in the prior art, and it is not obvious.

BRIEF DESCRIPTION OF THE DRAWINGS

The accompanying drawings required to be used in the description of the embodiments of the present disclosure or the related art are described briefly below, so that the technical solutions according to the embodiments of the present disclosure or according to the related art will become clearer. It is apparent that the accompanying drawings in the following description show only some embodiments of the present disclosure. For those skilled in the art, other accompanying drawings may also be obtained according to these drawings provided, without any creative work.

Parts corresponding to the reference signs: 1: scintillation crystal strip; 2: reflective material; 3: light guide sheet; 4: silicon photomultiplier tube; 5: output terminal; 6: total output terminal line; 7: preprocessing circuit; 8: silicon photomultiplier tube array; 9: high-reflectivity material block; 10: sanded rough surface of scintillation crystal strip; 11: sanded rough surface of light guide sheet; 12: adhered rough surface of scintillation crystal strip; 13: adhered rough surface of light guide sheet.

DETAILED DESCRIPTION

Preferred embodiments of the present disclosure will be described in detail below with reference to the accompanying drawings, so that the advantages and features of the present disclosure can be more easily understood by those skilled in the art, thereby making a clearer and definite definition of the scope of protection of the present disclosure.

First Embodiment

A PET detector for reducing the number of silicon photomultiplier tubes in use is provided, in which: the detector includes a layer formed by scintillation crystal array units and a layer formed by silicon photomultiplier tube array units respectively, the scintillation crystal array units and the silicon photomultiplier tube array units each have a rectangular cross section in the top view, and the top-view rectangular cross sections of the scintillation crystal array units and the silicon photomultiplier tube array units have the same area. Herein, the rectangular cross section is specifically a square cross section to facilitate cutting and placement.

Each scintillation crystal strip corresponds to exactly one pixel or one pixel array, which is a situation where it is easier to collect and calculate.

The scintillation crystal array unit is composed of a plurality of mutually parallel scintillation crystal strips, and the scintillation crystal strips are each rectangular parallelepipeds having the same specifications in terms of each of the length, the width and the height, each of which has the shape of a seal with a square cross section in the top view and being elongated in z-axis direction. Each two of the scintillation crystal strips are provided with a reflective material therebetween or surfaces of the scintillation crystal strips are plated with a reflective material. The reflective material is, for example, ESR.

The silicon photomultiplier tube array unit is an array aggregate with a rectangular cross section in the top view formed by arranging 16 silicon photomultiplier tube arrays. It is a 4*4 silicon photomultiplier tube array.

Figure 1:
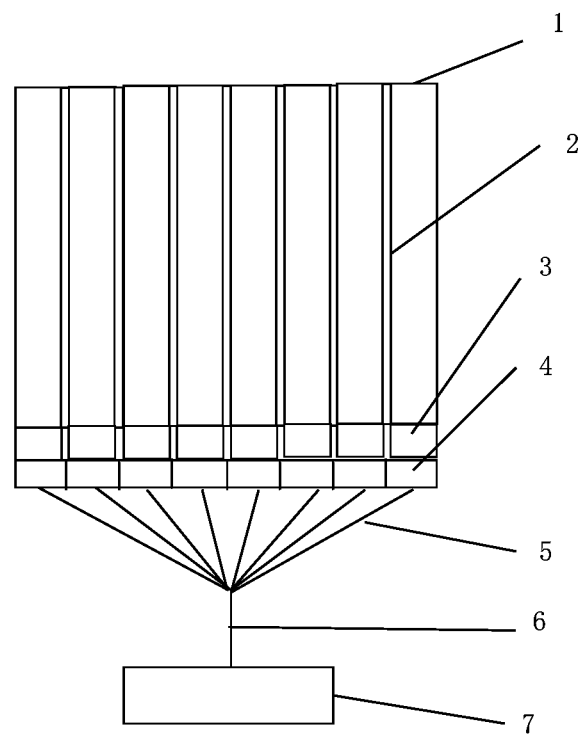
FIG. 1 is a schematic view of a side of a PET detector of the present application.
Figure 2:
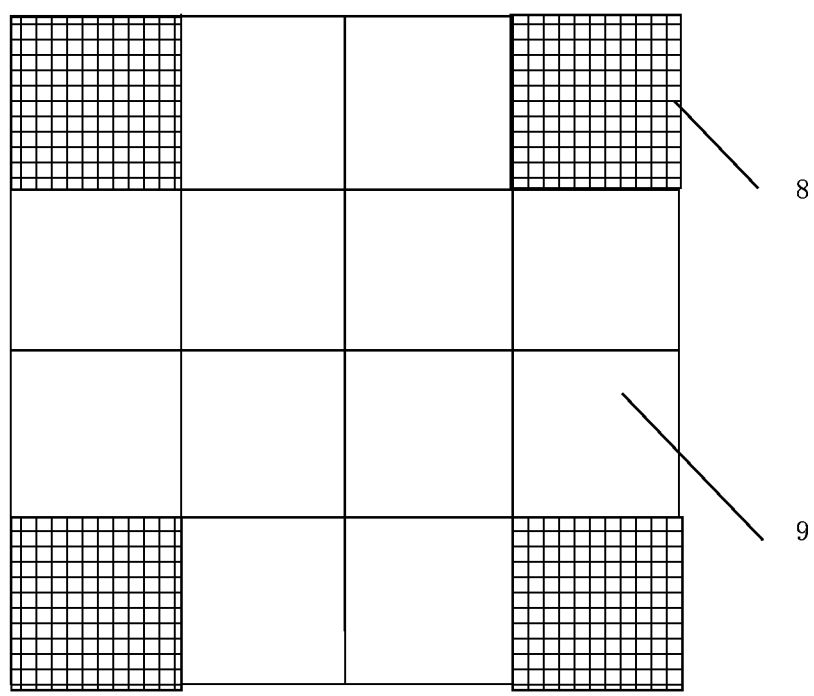
FIG. 2 is a schematic top view of a first situation in which N blocks in a silicon photomultiplier tube array unit in the PET detector of the present application are replaced with high-reflectivity material blocks.

12 blocks in the silicon photomultiplier tube array unit are replaced with high-reflectivity material blocks, which just corresponds to the situation in FIG. 2 showing that SiMPTs are located at the four corners. The high-reflectivity material block is integrally formed by using a mold adapted to the shape of the silicon photomultiplier tube array unit, or is formed by cutting. The high-reflectivity material block is made entirely of a uniform high-reflectivity material ESR, or a side of the high-reflectivity material block that faces the scintillation crystal array unit is coated with a high-reflectivity material ESR. The ESR is adhered to the main body of the light-transmitting material, and the light-transmitting material is, for example, a fluorine-containing polyester light-transmitting material, such as ETFE. The reflectivity of the side of the high-reflectivity material block that faces the scintillation crystal array unit is not less than 80%.

Herein, some silicon photomultiplier tube arrays are replaced with the high-reflectivity material, and this is based on the following principle: the existing PET image analysis does not and does not need to reach the image level of HD or even UHD; especially during the calculation, if the calculation is not performed separately for each pixel or each array of the silicon photomultiplier tube, but for each unit separately, then in fact, there is no need to wholly lay or apply silicon photomultiplier tubes. Herein, only part of the arrays needs to be replaced with the high-reflectivity material. For the case where the entire unit uses one circuit to form one signal output, it is herein sufficient to meet the needs, and the cost is also effectively controlled while meeting the needs. For the case where the unit is formed by 4*4 arrays, if only the four corners are reserved, the cost can be saved by 12/16; at the same time, the detection effect is not reduced or missing, and the original excited fluorescence can still be effectively captured. For the case of judging the condition of the disease through naked eyes, the resolution of the bitmap is not reduced.

Between the layers formed by the scintillation crystal array units and the silicon photomultiplier tube array units respectively, a layer formed by laying a plurality of light guide sheets flat is further formed. The plurality of light guide sheets are rectangular parallelepipeds of the same shape. The top-view cross section of the light guide sheets is a square. Providing the light guide layer not only plays a role in assisting light collection, but also produces an interaction for the case of replacing with the high-reflectivity material block. Herein, the fluorescence reflected by the high-reflectivity material block will basically not be reflected back into the crystals due to the characteristics of the light guides. Rather, it is basically ensured that after one or more reflections, the fluorescence will all be collected or received by other silicon photomultiplier tube arrays in the unit.

Further, the reflective material is selected from one of a super-grade retroreflective material, an engineering-grade reflective film, a high-grade reflective film, an enhanced spectrum reflective film, and a barium sulfate coating. The coating/plating made of the enhanced spectrum reflective film (ESR) has better effect in practice, and the cost is not high. All the positions between the scintillation crystal strips have the reflective material to avoid light doping.

Further, the top-view cross-sectional size of the light guide sheets is the same as that of the scintillation crystal strips, both being square. Each light guide sheet is aligned with the scintillation crystal strip in the top-view direction during installation; or the top-view cross-sectional size of the light guide sheets is the same as that of the silicon photomultiplier tube arrays, and each silicon photomultiplier tube is aligned with the scintillation crystal strip in the top-view direction during installation. This setting facilitates the calculation and arrangement in the early stage, and also facilitates the maintenance and adjustment in the later stage.

Further, for the contact surfaces of the layer formed by the scintillation crystal array units and the layer formed by laying the plurality of light guide sheets flat, the surfaces of all the scintillation crystal array units are rough surfaces, or the surfaces of all the light guide sheets are rough surfaces. The rough surfaces are all prepared by sanding or filing. The contact surfaces of the scintillation crystals and the light guides here may all be rough surfaces. This is a very important further improvement. This setting can further reduce the influence of light emitting positions on the basis of providing auxiliary light splitting by the light guides. For example, the high-reflectivity material block is located under the light guide sheet below a certain crystal strip, and this position is very far away from the nearest silicon photomultiplier tube array. In the absence of diffuse reflection on the rough surface of the light guide, multiple times of reflection may be required, and the multiple times of reflection cause its energy to be greatly attenuated, which has a very bad influence on the analysis; or a very large part of the light cannot reach the array in the collection time window, which has a great influence on the signal collection. The roughening of the surface is a very important auxiliary means for the general collection of optical signals, especially when part of the array is replaced by the high-reflectivity material block, so that it can be ensured that the effect of signal collection is not affected as much as possible when the array is replaced.

Second Embodiment

A PET detector for reducing the number of silicon photomultiplier tubes in use is provided, in which: the detector includes a layer formed by scintillation crystal array units and a layer formed by silicon photomultiplier tube array units respectively, the scintillation crystal array units and the silicon photomultiplier tube array units each have a rectangular cross section in the top view, and the top-view rectangular cross sections of the scintillation crystal array units and the silicon photomultiplier tube array units have the same area. Herein, the rectangular cross section is specifically a 1:2 rectangular cross section, and two scintillation crystal strips correspond to the area of one SiMPT to facilitate cutting and placement.

Every two scintillation crystal strips correspond to exactly one pixel or one pixel array, which is a situation where it is easier to collect and calculate.

The scintillation crystal array unit is composed of a plurality of mutually parallel scintillation crystal strips, and the scintillation crystal strips are each rectangular parallelepipeds having the same specifications in terms of each of the length, the width and the height, each of which has the shape of a half-seal with a 1:2 rectangular cross section in the top view and being elongated in z-axis direction. Each two of the scintillation crystal strips are provided with a reflective material therebetween or surfaces of the scintillation crystal strips are plated with a reflective material. The reflective material is, for example, ESR.

The silicon photomultiplier tube array unit is an array aggregate with a rectangular cross section in the top view formed by arranging 16 silicon photomultiplier tube arrays. It is a 4*4 silicon photomultiplier tube array.

Figure 3:
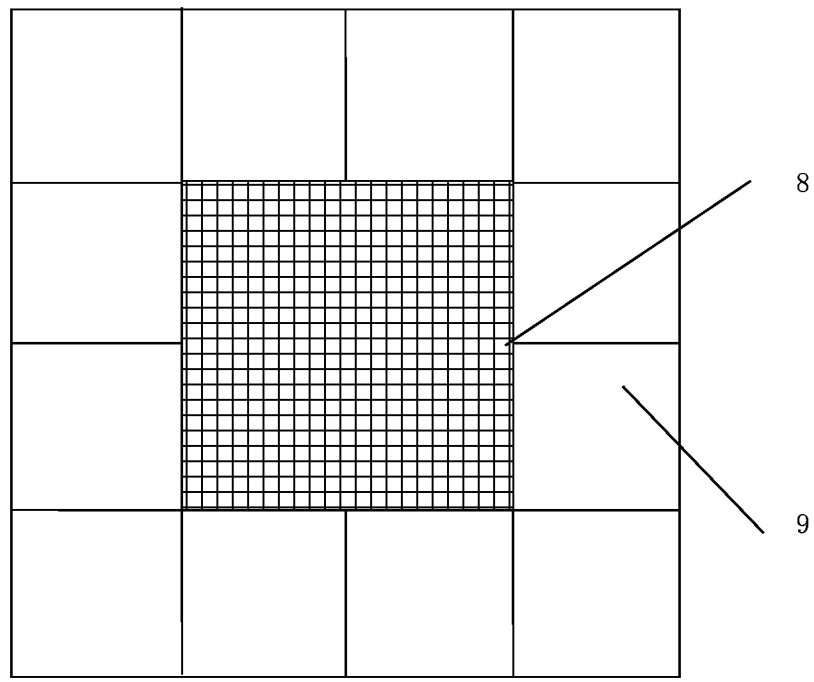
FIG. 3 is a schematic top view of a second situation in which N blocks in the silicon photomultiplier tube array unit in the PET detector of the present application are replaced with high-reflectivity material blocks.

12 blocks in the silicon photomultiplier tube array unit are replaced with high-reflectivity material blocks with the middle 4 blocks remaining unreplaced, which just corresponds to the situation in FIG. 3 showing that SiMPTs are located in the center. The high-reflectivity material block is integrally formed by using a mold adapted to the shape of the silicon photomultiplier tube array unit, or is formed by cutting. The high-reflectivity material block is made entirely of a uniform high-reflectivity material ESR, or a side of the high-reflectivity material block that faces the scintillation crystal array unit is coated with a high-reflectivity material ESR. The ESR is adhered to the main body of the light-transmitting material, and the light-transmitting material is, for example, a fluorine-containing polyester light-transmitting material, such as ETFE. The reflectivity of the side of the high-reflectivity material block that faces the scintillation crystal array unit is not less than 85%. Herein, the 12 blocks of ESR may also be directly made into a monolithic frame shape, and 2*2 SiMPTs are filled therein, thus saving labor and cost.

Herein, part of the silicon photomultiplier tube arrays is replaced with the high-reflectivity material. For the case where the unit is formed by 4*4 arrays, if only the middle 2*2 are reserved, the cost can be saved by 12/16; at the same time, the detection effect is not reduced or missing, and the original excited fluorescence can still be effectively captured. For the case of judging the condition of the disease through naked eyes, the resolution of the bitmap is not reduced.

Between the layers formed by the scintillation crystal array units and the silicon photomultiplier tube array units respectively, a layer formed by laying a plurality of light guide sheets flat is further formed. The plurality of light guide sheets are rectangular parallelepipeds of the same shape. The top-view cross section of the light guide sheets is a 1:2 rectangular shape, and the top view corresponds to the cross section of the scintillation crystal strips. Providing the light guide layer not only plays a role in assisting light collection, but also produces an interaction for the case of replacing with the high-reflectivity material block. Herein, the fluorescence reflected by the high-reflectivity material block will basically not be reflected back into the crystals due to the characteristics of the light guides. Rather, it is basically ensured that after one or more reflections, the fluorescence will all be collected or received by other silicon photomultiplier tube arrays in the unit.

Further, the reflective material is a barium sulfate coating. The coating/plating made of barium sulfate powder has better effect in practice, and the cost is not high. All the positions between the scintillation crystal strips have the reflective material to avoid light doping.

Further, the top-view cross-sectional size of the light guide sheets is the same as that of the scintillation crystal strips, both being a 1:2 rectangular shape. Each light guide sheet is aligned with the scintillation crystal strip in the top-view direction during installation; the top-view cross-sectional size of the light guide sheets is half that of the silicon photomultiplier tube pixels, and each silicon photomultiplier tube is aligned with the scintillation crystal strip in the top-view direction during installation. This setting facilitates the calculation and arrangement in the early stage, and also facilitates the maintenance and adjustment in the later stage.

Further, for the contact surfaces of the layer formed by the scintillation crystal array units and the layer formed by laying the plurality of light guide sheets flat, the surfaces of all the scintillation crystal array units are rough surfaces, or the surfaces of all the light guide sheets are rough surfaces. The rough surfaces are all prepared by adhering rough light guide materials, such as milky white translucent resin materials, or sanded translucent resin materials, such as polycarbonate light guide materials.

Third Embodiment

As shown in FIG. 2, it is possible to reserve only 4 corner blocks or pixel blocks at the corners in a 4*4 SiMPT array. In this way, since the pixels are small, in practice, it is only required to ensure that the signals collected by the PET bitmap are over a certain number, so that the recognition degree of PET images can still be ensured without reducing the technical effect. For example, 3000-5000 signals are reserved for the brain PET, and more than 8000-12000 signals are reserved for the whole-body PET, etc. The form of FIG. 2 can also be replaced to a small extent; for example, only the center 4 blocks are replaced, and the cost is saved by ¼ in this situation.

Fourth Embodiment

In FIG. 3, it is possible to reserve only the middle 2*2 blocks for each 4*4 unit. The advantage of this is that the middle 2*2 blocks can be a monolithic array of SiMPTs, and the 12 frame-shaped ESR or polyfluoroplastic coated with ESR on the sides can be formed integrally, which is very advantageous for processing. Even, it can be directly made into a monolithic block of ESR material, but 2*2 holes are reserved at equidistant positions. Each hole is filled with 2*2 SiMPTs, so that the preparation workload can be further reduced.

Fifth Embodiment

Figure 5:
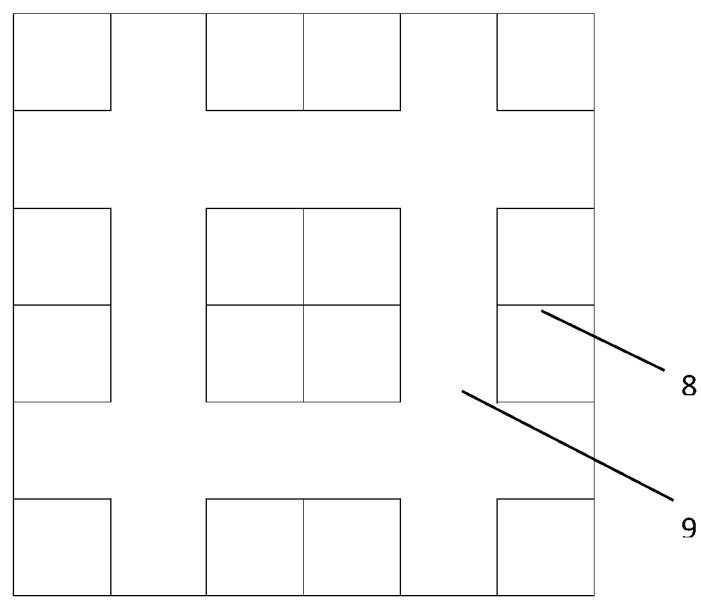
FIG. 5 is a schematic view showing that 5/9 of the SiMPTs is replaced with the high-reflectivity material blocks.

In FIG. 5, when P blocks in the silicon photomultiplier tube array unit are replaced with the high-reflectivity material blocks, a variety of configurations are possible. The isolated silicon photomultiplier tube array units may be at any distance from each other, as long as the signals can be received within a region. For the convenience of actual operation, the replacement may be specifically performed according to a certain ratio. For example, 5/9 or 1/2 of the silicon photomultiplier tubes are replaced, and the high-reflectivity blocks may be composed of several small pieces spliced together, or may be a whole piece. The vacant parts between the high-reflectivity blocks are filled with small silicon photomultiplier tubes or arrays. Taking FIG. 5 as an example, in fact, 5/9 of the SiMPT is replaced, and a pattern of regular replaced arrays is actually formed.

Sixth Embodiment

As stated for the fourth embodiment, the holes prepared for SiMPT can be freely changed between 1*1 and 10*10 according to the customized situation to adapt to the situation of SiMPT.

Seventh Embodiment

Figure 4:
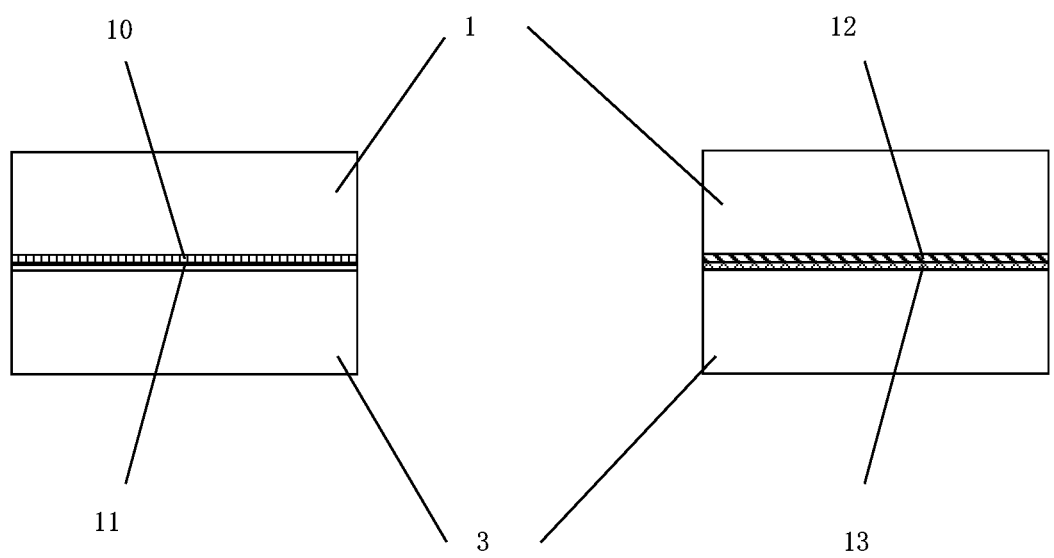
FIG. 4 is a detailed view of the connection between a scintillator crystal strip and a light guide sheet.

For the illustration in FIG. 4, in the left figure herein, the surfaces of all the scintillation crystal array units are rough surfaces, or the surfaces of all the light guide sheets are their own rough surfaces. In practice, a diffused light effect can be produced as long as one of the surfaces of the scintillation crystal strips and the light guide sheets is rough. The rough surfaces of the scintillation crystal strips can be achieved through a very fine file or similar tools, and the rough surfaces of the light guide sheets can be achieved through a file or similar tools, or integrally formed rough surfaces may be used during preparation, or commercially available products may be purchased.

Eighth Embodiment

For the illustration in FIG. 4, in the right figure herein, the surfaces of all the scintillation crystal array units are rough surfaces, and the rough surfaces are all formed by adhering a rough light guide material. In practice, a diffused light effect can be produced as long as one of the surfaces of the scintillation crystal strips and the light guide sheets is rough. Forming the rough surfaces of the scintillation crystal strips by adhering can avoid damage to the crystals. The material of the rough surfaces here may be selected from a variety of suitable materials. Translucent resin/plastic with a certain degree of heat resistance is preferred, and the polycarbonate material is a common material with high cost-effectiveness. Glass, although usable, is not the best choice due to insufficient toughness.

Ninth Embodiment

A PET detection method is provided, which utilizes the PET detector for reducing the number of silicon photomultiplier tubes in use as described above, and which includes the following steps: 1) taking each of the silicon photomultiplier tube arrays that have not been replaced as a current source, and connecting output terminals of all the silicon photomultiplier tube arrays that have not been replaced in parallel before outputting to total output terminal lines; 2) using the aforementioned PET detector for PET detection, preprocessing electrical signals obtained from the total output terminal lines through a preprocessing circuit, and then digitizing them to obtain output signals; 3) the output signals in step 2) being equivalent to an output signal collected under the situation where the entire silicon photomultiplier tube array unit is taken as an entire silicon photomultiplier tube array; and 4) collecting, by an operational terminal, all the output signals collected from all the aforementioned total output terminal lines, and analyzing the existence of LOR according to a preset correspondence to generate a PET image or a PET dynamic image. Herein, the situation of an entire silicon photomultiplier tube array specifically refers to a situation where there is no replacement, that is, it is considered that all the signals incident onto the entire replaced array are collected by the remaining SiMPTs.

Tenth Embodiment

A PET detection method is provided, which utilizes the PET detector for reducing the number of silicon photomultiplier tubes in use as described above, and which includes the following steps: 1) taking each of the silicon photomultiplier tube arrays that have not been replaced as a current source, and connecting output terminals of all the silicon photomultiplier tube arrays that have not been replaced in parallel before outputting to total output terminal lines; 2) using the aforementioned PET detector for PET detection, preprocessing electrical signals obtained from several adjacent total output terminal lines through a preprocessing circuit, and then digitizing them to obtain output signals; 3) the output signals in step 2) being equivalent to an output signal collected under the situation where all the photomultiplier tube array units corresponding to the several adjacent total output terminal lines in step 2) are taken as a separate collection unit; and 4) collecting, by an operational terminal, all the output signals from all the separate collection units obtained through collection, and analyzing the existence of LOR according to a preset correspondence to generate a PET image or a PET dynamic image.

In fact, after the above replacement, the replaced SiMPT array layer is automatically formed. This layer is composed of very small repeated basic units, such as the partially replaced part in the above 4*4. If permitted by the resolution, the aforementioned units can be further combined to collect signals, such as collecting the signals of 2*2, 3*3 and 2*3 basic units, as long as the resolution of the final PET bitmap is sufficient for resolving. The burden and cost of the electrical parts can be further reduced, and the complexity of the line can be reduced.

Described above are only specific embodiments of the present disclosure, but the scope of protection of the present disclosure is not limited to this. Any change or replacement that can be contemplated without creative work should be covered within the scope of protection of the present disclosure. Therefore, the scope of protection of the present disclosure shall be accorded with the scope of the claims.

The invention claimed is:

1. A PET detector for reducing the number of silicon photomultiplier tubes in use, wherein:
  the detector comprises a layer formed by scintillation crystal array units and a layer formed by silicon photomultiplier tube array units respectively, the scintillation crystal array units and the silicon photomultiplier tube array units each have a rectangular cross section in the top view, and the top-view rectangular cross sections of the scintillation crystal array units and the silicon photomultiplier tube array units have the same area;
  the scintillation crystal array unit is composed of a plurality of mutually parallel scintillation crystal strips, the scintillation crystal strips are each rectangular parallelepipeds having the same specifications in terms of each of the length, the width and the height, and each two of the scintillation crystal strips are provided with a reflective material therebetween or surfaces of the scintillation crystal strips are plated with a reflective material;
  the silicon photomultiplier tube array unit is an array aggregate with a rectangular cross section in the top view formed by arranging M silicon photomultiplier tube arrays;
  N blocks in the silicon photomultiplier tube array unit are replaced with high-reflectivity material blocks, and the high-reflectivity material block is integrally formed by using a mold adapted to the shape of the silicon photomultiplier tube array unit, or is formed by cutting; the high-reflectivity material block is made entirely of a uniform high-reflectivity material, or a side of the high-reflectivity material block that faces the scintillation crystal array unit is coated with a high-reflectivity material, and the reflectivity of the side of the high-reflectivity material block that faces the scintillation crystal array unit is not less than 50%; and
  both M and N are natural numbers greater than 1, and M−N≥1.

2. The PET detector for reducing the number of silicon photomultiplier tubes in use according to claim 1, wherein:
  between the layers formed by the scintillation crystal array units and the silicon photomultiplier tube array units respectively, a layer formed by laying a plurality of light guide sheets flat is further formed, the plurality of light guide sheets are rectangular parallelepipeds of the same shape, and the top-view cross section of the light guide sheets is rectangular; and the reflective material is selected from one of a super-grade retroreflective material, an engineering-grade reflective film, a high-grade reflective film, an enhanced spectrum reflective film, and a barium sulfate coating.

3. The PET detector for reducing the number of silicon photomultiplier tubes in use according to claim 2, wherein: the top-view cross-sectional size of the light guide sheets is the same as that of the scintillation crystal strips, and each light guide sheet is aligned with the scintillation crystal strip in the top-view direction during installation; or the top-view cross-sectional size of the light guide sheets is the same as that of the silicon photomultiplier tube arrays, and each silicon photomultiplier tube is aligned with the scintillation crystal strip in the top-view direction during installation.

4. The PET detector for reducing the number of silicon photomultiplier tubes in use according to claim 2, wherein: for the contact surfaces of the layer formed by the scintillation crystal array units and the layer formed by laying the plurality of light guide sheets flat, the surfaces of all the scintillation crystal array units are rough surfaces, or the surfaces of all the light guide sheets are rough surfaces.

5. The PET detector for reducing the number of silicon photomultiplier tubes in use according to claim 4, wherein: the rough surfaces are all prepared by sanding or filing, or a substance that makes the surfaces rough but still be transparent to light is coated or adhered to the surfaces.

6. A PET detection method, which utilizes the PET detector for reducing the number of silicon photomultiplier tubes in use according to claim 2, and which comprises the following steps:
1) Taking each of the silicon photomultiplier tube arrays that have not been replaced as a current source, and connecting output terminals of all the silicon photomultiplier tube arrays that have not been replaced in parallel before outputting to total output terminal lines;
2) Using the PET detector for PET detection, preprocessing electrical signals obtained from the total output terminal lines through a preprocessing circuit, and then digitizing them to obtain output signals;
3) The output signals in step 2) being equivalent to an output signal collected under the situation where the entire silicon photomultiplier tube array unit is taken as an entire silicon photomultiplier tube array; and
4) Collecting, by an operational terminal, all the output signals collected from all the total output terminal lines, and analyzing the existence of LOR according to a preset correspondence to generate a PET image or a PET dynamic image.

7. A PET detection method, which utilizes the PET detector for reducing the number of silicon photomultiplier tubes in use according to claim 2, and which comprises the following steps:
1) Taking each of the silicon photomultiplier tube arrays that have not been replaced as a current source, and connecting output terminals of all the silicon photomultiplier tube arrays that have not been replaced in parallel before outputting to total output terminal lines;
2) Using the PET detector for PET detection, preprocessing electrical signals obtained from several adjacent total output terminal lines through a preprocessing circuit, and then digitizing them to obtain output signals;
3) The output signals in step 2) being equivalent to an output signal collected under the situation where all the photomultiplier tube array units corresponding to the several adjacent total output terminal lines in step 2) are taken as a separate collection unit; and
4) Collecting, by an operational terminal, all the output signals from all the separate collection units obtained through collection, and analyzing the existence of LOR according to a preset correspondence to generate a PET image or a PET dynamic image.

* * * * *